United States Patent [19]

Kawamura et al.

[11] Patent Number: 5,183,744
[45] Date of Patent: Feb. 2, 1993

[54] CELL HANDLING METHOD FOR CELL FUSION PROCESSOR

[75] Inventors: Yoshio Kawamura, Kokubunji; Shinji Tanaka, Akishima; Kazuo Sato; Kenko Uchida, both of Tokyo; Hiroyuki Kohida, Fuchu, all of Japan

[73] Assignee: Hitachi, Ltd., Tokyo, Japan

[21] Appl. No.: 425,028

[22] Filed: Oct. 23, 1989

[30] Foreign Application Priority Data

Oct. 26, 1988 [JP] Japan .............................. 63-268030
Nov. 11, 1988 [JP] Japan .............................. 63-283601

[51] Int. Cl.⁵ ..................... A01N 1/02; C12Q 1/24; C12M 3/02
[52] U.S. Cl. ............................... 435/30; 435/2; 435/286
[58] Field of Search ............. 435/2, 300, 301, 310, 435/311, 284, 285, 286, 30

[56] References Cited

U.S. PATENT DOCUMENTS

| | | | |
|---|---|---|---|
| 4,480,038 | 10/1984 | Cheng | 435/261 |
| 4,649,109 | 3/1987 | Perlman | 435/182 |
| 4,729,949 | 3/1988 | Weinreb et al. | 435/173 |
| 4,894,343 | 7/1990 | Tanaka et al. | 435/300 |
| 4,895,805 | 1/1990 | Sato et al. | |

OTHER PUBLICATIONS

Morikawa, H. "Electric Fusion . . . ", Saboo Koogaku, vol. 3, No. 6, pp. 479-505 (Translation of Reference 3 on Information Disclosure statement of Oct. 23, 1989).
Tanaka, N. et al. "Research of Micro Mechanics . . . ", Proceedings of Sprg. Conference of Japan Society of Precision Engineering 1987, pp. 845-846. (Translation of Reference 1).
Freifelder, D., *Molecular Biology.*, Boston, Jones and Bartlett Publislers, 1987, pp. 70-71.
Proceedings of Spring Conference of the Japan Society of Precision Engineering, 1987, pp. 845-846.
Saibo Kogaku (Cell Technology), vol. 3, No. 6, pp. 497-505

Primary Examiner—Douglas W. Robinson
Assistant Examiner—Timothy J. Reardon
Attorney, Agent, or Firm—Antonelli, Terry, Stout & Kraus

[57] ABSTRACT

A method and an apparatus for the treatment of particles or biological cells are disclosed, wherein the particles or cells are precipitated or ascended depending on the specific gravity of a liquid used, and the particles or cells are handled with the aid of a holding plate. A method and an apparatus for the fusion of particles or cells are also disclosed, wherein an electric voltage is loaded on a position between electrodes in a microchamber to fuse the particles or cells held in the microchamber.

3 Claims, 9 Drawing Sheets

CELL HANDLING METHOD FOR CELL FUSION PROCESSOR

BACKGROUND OF THE INVENTION

The present invention relates to an apparatus for the treatments of particles and biological cells. Particularly, the invention relates to a method of handling particles, a cell treatment equipment and a cell fusion processor.

An apparatus is known from Proceedings of the Spring Conference of the Japan Society of Precision Engineering, 1987, pages 845-846, and U.S. patent application Ser. No. 122,269 filed on Nov. 18, 1987, which apparatus is so designed that one pair each of different kind cells are supplied to each of microchambers arranged in a matrix-like pattern and are absorbed and held in a small aperture of the microchamber with the aid of an absorption nozzle and that the cell pair is then subjected to a cell treatment operation in each microchamber.

According to the prior art, use is made of a flowcell to pour cells into the microchamber at a rate of one cell at a time so as to provide a pair of the cells. According to this procedure, it is difficult to treat a large amount of cells for a short period of time and also to maintain the activity of the cells.

SUMMARY OF THE INVENTION

It is an object of this invention to provide a method and an apparatus for the treatment of a large amount of biological cells, wherein the cells are held and handled while the activity of the cells is maintained.

To attain this object, there is provided a method wherein particles or biological cells are supplied and held in microchambers with the aid of a solution having a specific gravity different from that of the particles or the cells and then the particles or the cells are handled. More specifically, there is provided a method of handling a large amount of particles or cells in microchambers, wherein a container is charged with such a large amount of particles or cells and also charged with a first isotonic solution having a specific gravity greater than that of the particles or the cells, so that the particles or the cells will move upwards and flow on a trapped plane and the floating particles or cells are absorbed and held. Thereafter, the container is charged with a second isotonic solution having a specific gravity smaller than that of the particles or the cells, whereby the uncollected particles or the uncollected cells sink away from the trapped plane. The collected particles or cells are transferred to the microchambers and held therein. Thereafter, the above procedures are again carried out for different kinds of particles or cells, whereby a pair of different kind of particles or cells can be handled in one and the same microchamber.

Also, there is another method of injecting a large amount of particles or cells to microchambers, wherein use is made of a means for supplying the particles or the cells to a container. The container is charged with a first isotonic solution having a specific gravity smaller than that of the particles or the cells. A platelike holding means is used which has absorption ports absorbing and holding the resultant precipitated particles or cells. A second isotonic solution having a specific gravity greater than that of the particles or the cells is injected into the container, whereby the untrapped particles or cells will ascend away from the holding plane. The desired particles or cells are held on the plane-like holding means. Then the particles or cells are transferred to microchambers by a handling means. The above-mentioned operations are again carried out for other kinds of particles or cells, so that these kinds of particles or cells are accommodated in the microchambers in such a manner that one pair of these kinds of particles or cells are accommodated in one and the same microchamber.

In order to effect a cell fusion operation of pairs of two different cells for a short period of time, it is possible to employ the cell handling means mentioned above, microchamber means provided with an electrode, and a means for the electric voltage control.

According to this invention, the cells are held on the plate-like holding means having a plurality of the absorption ports. To enhance the cell holding efficiency, it is necessary to increase the cell dispersion density of the isotonic solution present near the absorption ports. On the other hand, after a desired amount of the cells have been held in the holding means, it is desirable that any excess cells are not present near the absorption ports, and, in other words, it is necessary to decrease the cell dispersion density of the isotonic solution present near the absorption ports.

According to this invention, use is made of isotonic solutions having different specific gravities. When cells are supplied to an isotonic solution having a specific gravity higher than that of the cells, the cell will move upwards and float on the surface of the platelike holding means in the isotonic solution. On the other hand, the cells will sink downwards in an isotonic solution having a specific gravity smaller than that of the cells. Based on this principle, it is possible to control the dispersion density of the cells in an isotonic solution present near the absorption ports. As a result of this control, the holding rate of the absorption ports will increase, and the number of undesired cells near the ports will be very small, so that the desired cells can be transferred to the treatment means at a high transfer rate, and consequently it is sure that pairs of different cells can be formed in a large amount for a short period of time.

DETAILED DESCRIPTION OF THE PREFERRED EMBODIMENTS

Figure 2:
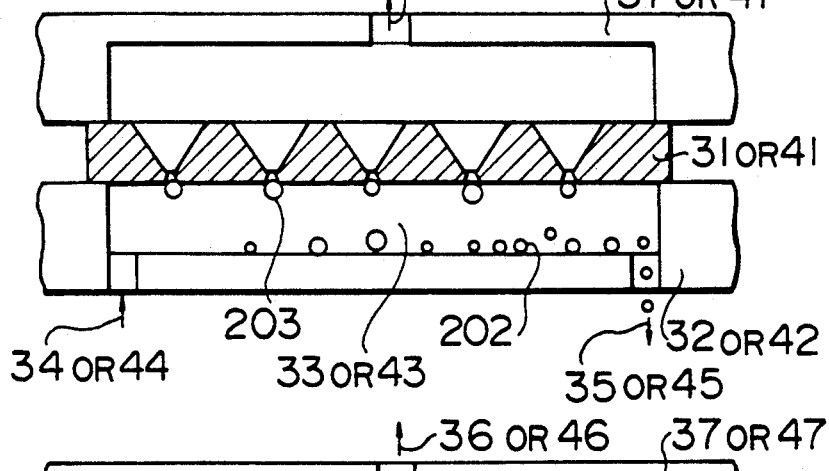
FIG. 2 is an enlarged view illustrating another embodiment of this invention.
Figure 3:
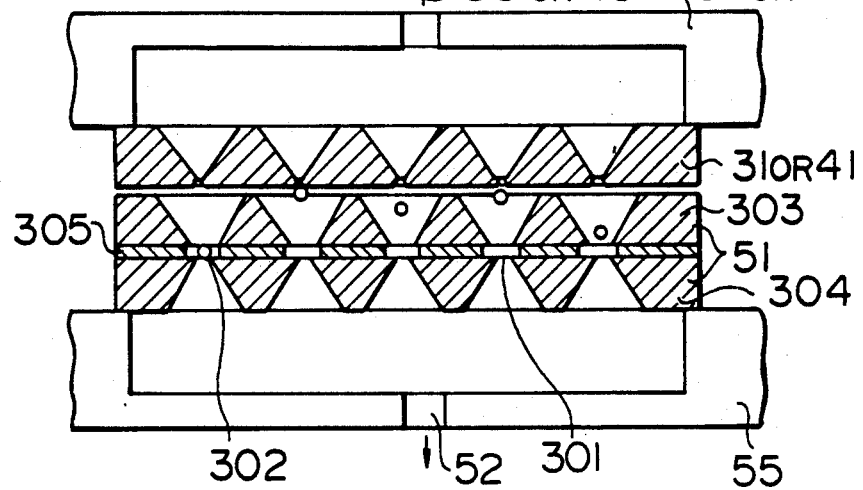
FIG. 3 is an enlarged view illustrating the functions of this invention.

An explanation will be made about certain embodiments of this invention with reference to FIGS. 1 to 3. In these embodiments, use is made of biological cells having a size of about 20 μm to 100 μm. In the drawings, the same components are represented by the same reference numerals. The arrow mark given in the drawings indicates the flow direction of the isotonic solutions.

Figure 1:
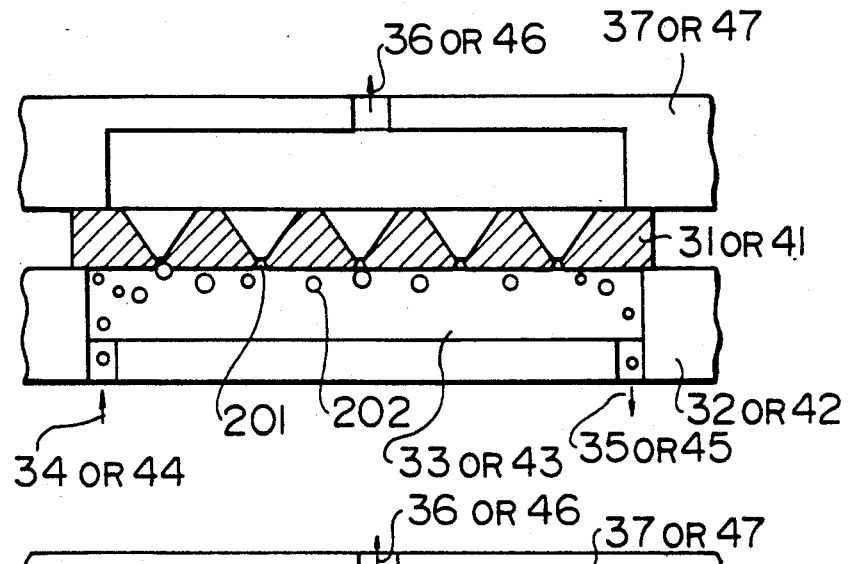
FIG. 1 is an enlarged view illustrating an embodiment of this invention.

In FIG. 1, there are shown a holding means 31 or 41, a holder thereof 37 or 47, and a supply means 32 or 42 which are placed in a second isotonic solution contained in a container (not shown). The holding means 31 or 41 can be produced by a process, wherein a number of absorption ports 201 having a size of 10 μm × 10 μm are formed at intervals of 770 μm with a matrix-like pattern on an Si wafer with a thickness of 360 μm according to a semiconductor processing technique. A predetermined gap 33 or 43 is made between the supply means 32 or 42 and the holding means 31 or 41. The gap 33 or 43 serves as a lane for flowing the isotonic solution admixed with the cells 202. The size of gap 33 or 43 may be 300 μm in consideration of the lane resistance.

The supply means 32 or 42 is provided with a supply port 34 or 44 and an exhaust port 35 or 45. From the supply port 34 or 44, a suspension of cells in the first isotonic solution is supplied to this apparatus.

The second isotonic solution has a specific gravity smaller than that of the cells, so that the cells will sink down in the second solution. The first isotonic solution has a specific gravity greater than that of the cells, so that the cell will float on the surface of the holding means in the first solution. In order to handle the cells without any decrease of the activity of the cells, use may be made of 0.5 mole sorbitol solution as the second isotonic solution. As the first isotonic solution, it is possible to use 0.5 mole sucrose solution.

The cells, which have been supplied to the gap 33 or 43 are then held in the absorption ports 201 at a rate of one cell per one port, under an absorption pressure applied thereto through a pipe connector 36 or 46. In order to hold the cells in the ports without giving any adverse effect on the cell activity, it is necessary to apply a low absorption pressure of about 5 to 50 mmAq, so that it is not probable that the cells which are not present near the absorption ports 201 will be absorbed in the ports 201. If the concentration of the cells suspended in the isotonic solutions near the absorption ports 201 is low, the cell absorption efficiency of the absorption ports 201 will be undesirably low. According to this invention, it is possible to use the first isotonic solution to float the cells on the surface of the holding means, whereby the cells will be brought in contact with the holding means 31 or 41, so that the concentration of the cells in the isotonic solution present near the absorption ports 201 will increase. As a result of this, the holding efficiency will be enhanced. It has been observed that the holding efficiency obtained by using the first isotonic solution according to this invention is three times higher than that obtained in the case where the first isotonic solution is not used.

After the holding means has held the cells in the absorption ports 201 at a rate of one cell per one port, any excess cells are unnecessary, and therefore it is desirable to decrease the concentration of the cells suspended in the isotonic solution present near the absorption parts. According to this invention, this purpose is accomplished by passing a stream of the second isotonic solution through the gap 33 or 43 during the cleaning operation after the holding operation. FIG. 2 shows the behavior of the cells during the cleaning operation, wherein the excess cells 202 are moved downwards away from near the surface of the holding means, so that such excess cells are no longer present near the absorption ports after the absorption ports 201 have held the desired cells 203 therein. In the manner shown above, the desired cells are effectively held in the holding means. Referring to the above, it is noted that there are the formulas:

[Precipitation force]

= [Specific gravity difference] × [cell volume]

[Absorption force]

× [Area of absorption port] × [Absorption pressure difference]

The undesirable removal of the cells from the absorption ports can be avoided, if there is kept the following relationship:

[precipitation force] < [Absorption force]

Figure 4:
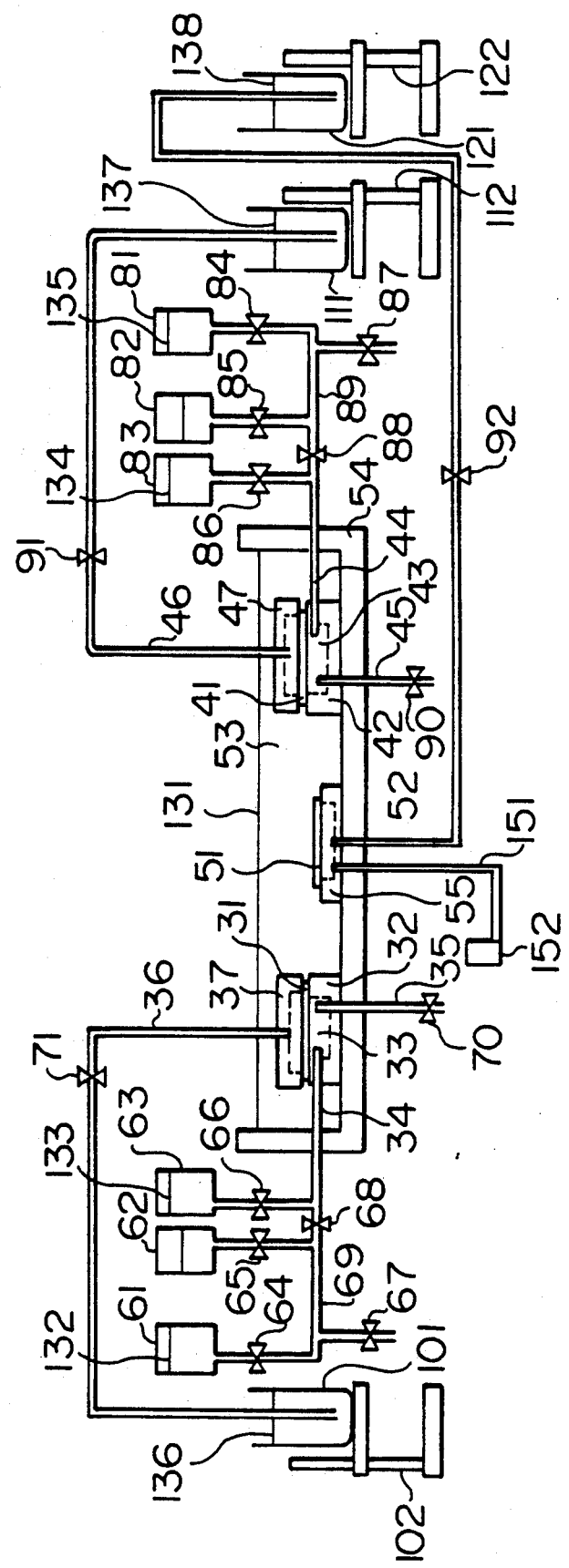
FIG. 4 is an illustrative view of a cell fusion processor according to this invention.

As for a process of transferring the held cells to a treatment means, an explanation will be made with reference to FIG. 3. In FIG. 3, there is shown the treatment means 51 in a position close to the holding means 31 or 41, these two means being soaked in the isotonic solution 53 (FIGS. 4 and 5). The treatment means 51 may be produced by a method, wherein a number of apertures 301 having a size of 10 μm × 100 μm are formed in a matrix-like pattern at intervals of 770 μm in an Si wafer with a thickness of 360 μm, according to a semiconductor processing technique as in the case of the absorption ports 201 of the holding means. The Si wafer having the apertures 301 formed therein is placed on a member 304 to form the electrode portion 305. The microchambers 303 is disposed on the electrode portion 305 so as to form the treatment means 51.

The cells held in the holding means can be transferred into the apertures 301 of the treatment means 51 in a manner, wherein a positive pressure is applied to the holding means instead of the absorption pressure and the treatment means is kept under an absorption pressure of about several mmAq applied thereto through a conduit 52 disposed in the holder 55. The reference number 302 represents a cell arrived at the aperture 301, while other several cells which are falling down are also shown in FIG. 3.

After the cells have been transferred into the microchambers at a rate of one cell per one microchamber, the other kind of cells are held in the holding means, and then transferred into the treatment means, so that each microchamber is occupied by a pair of these different cells. Thus, the cell pairs are positioned between the two electrodes mentioned above, so that it is possible to effect a cell fusion operation by applying an electrical voltage between the electrodes.

A detailed description is given for a method of individually fusing the cell pairs which have entered the treatment means, and also for a method of observing the cells in the course of the cell fusion.

Figure 6:
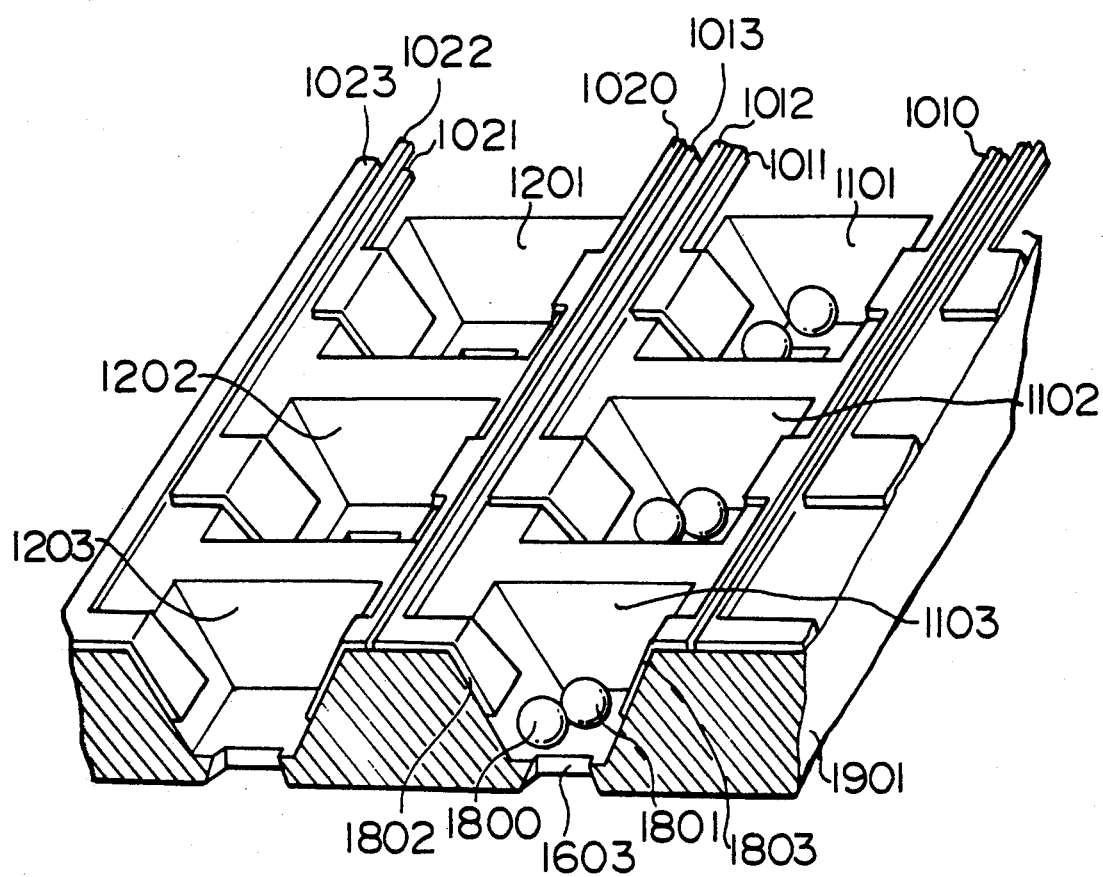
FIG. 6 is a perspective view of a cross section of a treatment means employed in this invention.
Figure 7:
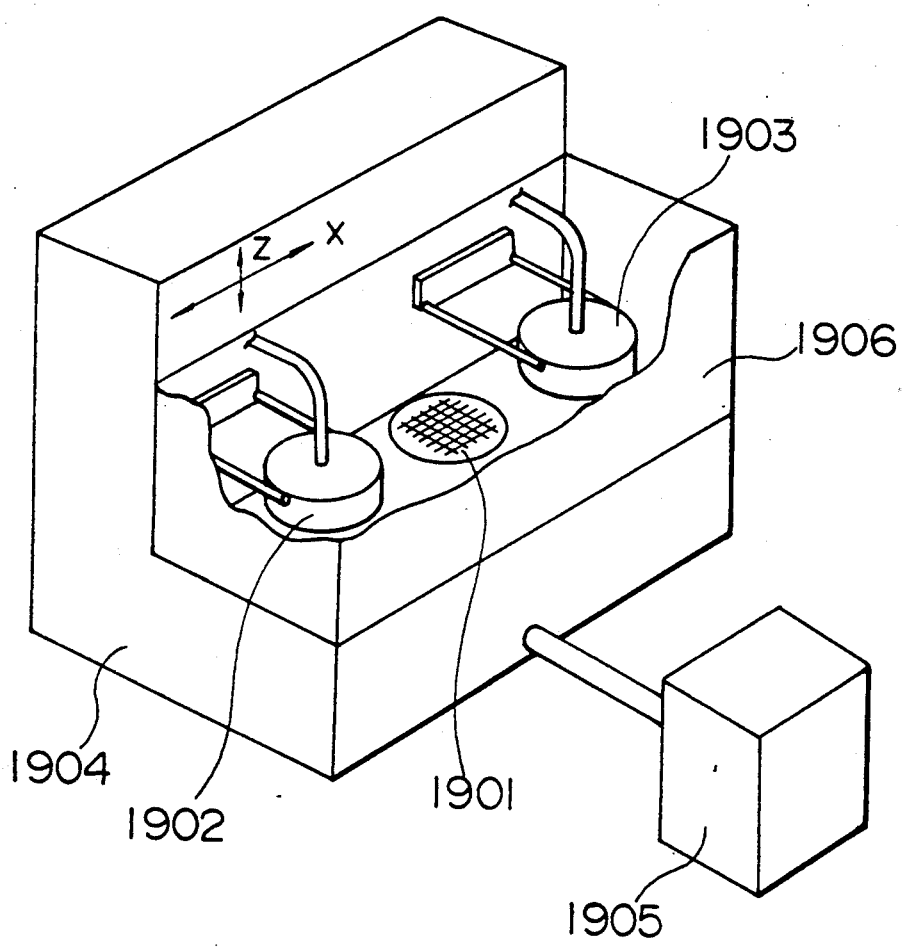
FIG. 7 is a perspective view of a cell fusion processor according to this invention.
Figure 8:
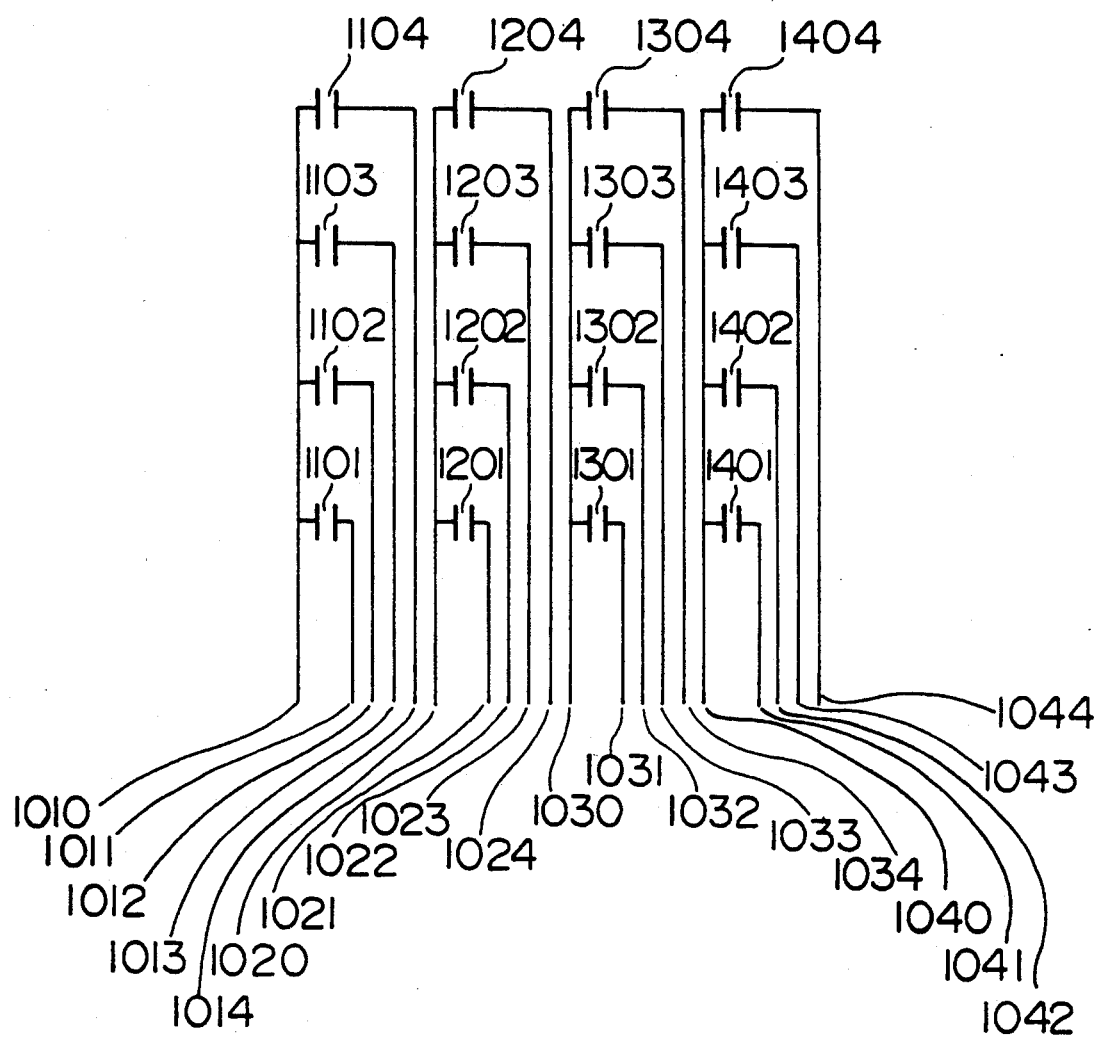
FIG. 8 is an electrical wiring diagram employed in an embodiment of this invention.

FIG. 6 illustrates a microchamber plate employed as the above-mentioned treatment means. FIG. 7 shows a cell fusion processor employing the microchamber plate. FIG. 8 is a wiring diagram for the electrodes disposed in the microchamber plate. In FIGS. 6 to 8, the same components are represented by the same reference numerals. More specifically, FIG. 6 shows a bird's-eye view of the cross section of the microchamber plate for handling cells having a size of 20 to 100 μm as the particles. The microchamber plate 1901 can be produced by a method, wherein an Si wafer having a thickness of 400 μm is subjected to an anisotropic etching operation so as to form the microchambers 1101 to 1103 and 1201 to 1203 arranged in a matrix-like pattern at a pitch of 770 μm. In each of the microchambers 1101 to 1103, a pair of the two different cells 1800 and 1801 are held under an absorption pressure. FIG. 6 shows the microchambers 1201 to 1203 which are not filled with the cells. These microchambers each have an absorption port as represented by the absorption port 1603 of the microchamber 1103. These absorption ports have the same structure. An absorption means (not shown) is employed to apply an absorption force to the microchambers, so that the cells can be kept in the microchambers.

A container 1906 (FIG. 7) is charged with an isotonic solution. By the cell handling means 1902 and 1903 (FIG. 7), a predetermined number of cells are transferred to the microchambers. The microchamber 1103 is provided with one set of electrodes 1802 and 1803, which are electrically connected via lead wires 1010 and 1013 to an electric control unit 1905 (FIG. 7). The other microchambers 1101, 1102 and 1201 to 1203 are also provided with electrodes, which are connected via lead wires 1011, 1012 and 1020 to 1023 to the electric control unit in such a way that an electric voltage can be independently applied to each electrode and that an electric voltage measurement can be carried out.

FIG. 7 is a perspective view of a cell fusion processor 1904 employing the microchamber plate 1901 shown in FIG. 6. A container 1906 is filled with 0.5 mole isotonic sorbitol solution, which can provide an osmotic pressure sufficient to maintain the cell activity. The processor has a cell handling means 1902 for a cell A and another handling means 1902 for a different cell B. These cell handling means each have absorption cavities at the positions corresponding to the positions of the microchambers of the microchamber plate 1901, so that one of the two different cells A and B can be firstly transferred into each microchamber and that the remaining one of the cells A and B can be then transferred into each microchamber in order to place one pair of the cells A and B in each microchamber. The cell handling means 1902 and 1903 are so designed that they can move in the directions X and Z. By the cell handling operation mentioned above, one pair of the cells A and B are supplied and kept in each microchamber of the microchamber plate. Each microchamber is individually provided with the two electrodes, which are electrically connected via lead wires to the electric control unit 1905. The electric control unit 1905 comprises an electric power source necessary for the cell fusion operation of the cells placed in the microchamber plate; and a control circuit which receives a voltage change measured between the electrodes as an indication of the behavior of the cells held between the electrodes, and which regulates the electric voltage, depending on the behavior of the cells. The electric control unit 1905 also has a circuit for driving and controlling the cell handling means 1902 and 1903 to transfer the cells to the microchamber plate and furthermore has a switch means for these circuits.

FIG. 8 shows a planar wiring pattern, wherein the electrodes 1101 to 1104, 1201 to 1204, 1301 to 1304 and 1401 to 1404 are disposed together with the lead wires 1010 to 1014, 1020 to 1024, 1030 to 1034 and 1040 to 1044.

An explanation will be made about an example of an electrical operation of the biological cell fusion. In this example, the cells which have been held in the microchamber 1103 shown in FIG. 6 are subjected to the cell fusion operation. The cells 1800 and 1801 are contacted with each other in the absorption aperture 1603 under an absorption pressure applied thereto. The absorption aperture 1603 has an elongated shape and is disposed between the two electrodes, so that the cells are contacted with each other in the shape of letter 8-like, the longitudinal axis of which is parallel to the direction of the electric field. After the two cells have been brought into contact with each other, an electric pulse voltage is loaded between the electrodes, so that a fusion will begin at the cell membranes of the two cells contacted with each other. As the fusion proceeds, the shape of the two cells contacted with each other changes through a snowman-like shape and then through an ellipsoidal shape into a spherical shape. The electrical resistance, the electrostatic capacity and the amount of electrical charges between the electrodes may vary depending on the shape change of the cells.

If it is assumed that the cell with a radius $r_1$ are fused together with another cell with a radius $r_2$ to form a fused cell product with a radius of $r_3$, the following relationship is derived, because the total volume of the two cells are kept constant.

$$r_1^3 + r_2^3 = r_3^3$$

The maximum length of the two cells contacted is:

$$2 \cdot (r_1 + r_2)$$

The maximum length of the fused cell product is:

$$2 \cdot r_3 = 2 \cdot (r_1^3 + r_2^3)^{\frac{1}{3}}$$

For instance, if the two cells have the same radius R, the maximum length of the two cells contacted with each other is 4R. After the two cells have been fused, the resultant fused spherical product has a radius of: $2^{\frac{1}{3}} \cdot R = 1.26R$. Namely, the maximum length of the fused spherical product is 2.52R. Thus, the maximum length of the fused spherical product is only 63% of the maximum length of the two unfused cells contacted with each other. This length change can be detected as an electrical potential change between the electrodes.

After an electrical pulse voltage has been loaded for a biological cell fusion, it is examined whether there is a change of the voltage between the two electrodes. The cell fusion is accompanied with a change of the electrical potential. After the fused spherical product has been formed as a result of the cell fusion, the electrical potential change will be rather small. Therefore, it is possible to determine the starting point of the cell fusion by a method, wherein an electrical pulse voltage is loaded on a pair of cells to be fused together and a measurement is carried out about the electrical potential between the two electrodes so as to observe the potential change. Until the cell fusion has begun, the electrical pulse voltage is continuously loaded on the cells at a suitable loading cycle. If the cells are not fused under the conditions mentioned above, it is recommended to change the operational conditions by continuously raising the electrical pulse voltage to be loaded, whereby the cells can be fused together. After the start of the cell fusion has been detected by the observation of the electrical potential change, the loading of the electrical pulse voltage for the cell fusion is turned off. If use is made of cells having a low activity, the cells will sometimes be broken by the loading of the electrical pulse voltage thereon. In such a case, there is observed a particular mode of the electrical potential change, wherein a sudden voltage change has occurred before a constant potential is observed. This mode is distinguishable from a cell fusion mode, wherein a gradual change of the electrical potential occurs as the cell fusion proceeds. In this way, it is possible to determine when a breakage of the cells has occurred.

If it is observed that one of the two cells has been damaged, the remaining cell should not be kept alive alone, because the remaining cell might proliferate in the course of a later cultivation stage. In order to destroy the remaining cell, a high electric voltage should be loaded thereon. By observing the electrical potential change, it is possible to detect not only the presence or absence of the remaining cell but also the destruction of the remaining cell. According to the method mentioned above, it is possible to keep only the desired fused cell products in the processor.

A description is given for an example of the cell fusion process for cells of lettuce. In this example, the distance between the two electrode is 200 μm, and use is made of a 0.5 mole sorbitol solution. The cell fusion begins after an electrical pulse voltage (about 25 V; 150 us) has been loaded, with the proviso that the loading operation is effected one time or at most several times. As the cell fusion proceeds, the shape of the two cells contacted with each other changes from a shape like letter 8 through a snowman like shape and then through an ellipsoidal shape into a spherical shape for a period of time of about 2 to 3 minutes.

Figure 9:
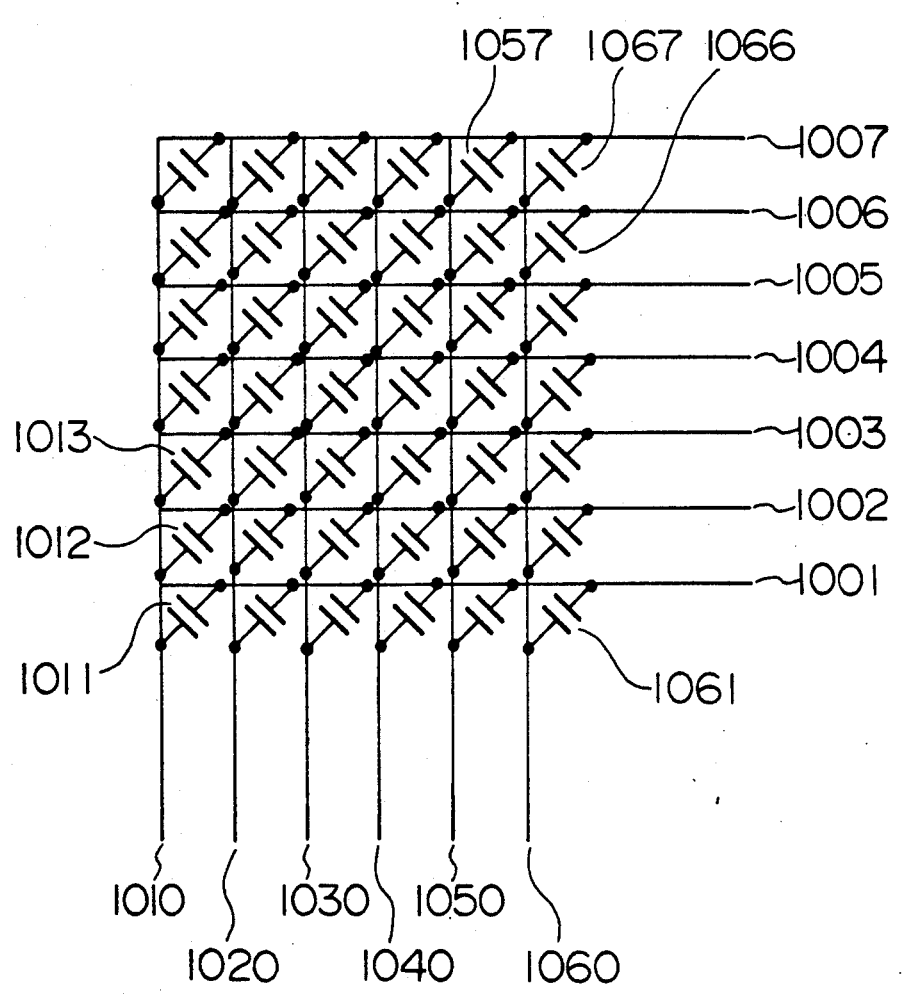
FIG. 9 is an electrical wiring diagram employed in another embodiment of this invention.

The electrical wiring pattern shown in FIGS. 6 and 8 does not contain any crossing points, so that a patterning operation of this circuit is rather simple. However, there is a limitation on the number of microchambers formed on the chamber plate. FIG. 9 is a schematic view of another example of such wiring patterns. In this pattern, there are the wires 1010 to 1060 in the direction Y and the wires 1001 to 1007 in the direction X, so that the former wires cross the latter wires without contacting at the crossing points. Plural sets of two electrodes 1011 to 1067 each are connected to the lead wires in the positions near the crossing points in the manner illustrated in FIG. 9. It is easy for a skilled person in the art to load an electrical voltage on each electrode and to measure the electrical potential between each set of the electrodes, because the wiring pattern shown in FIG. 9 is similar to that customarily employed in two dimensional liquid crystal devices, two dimensional MOS imaging sensers and the like.

Figure 10:
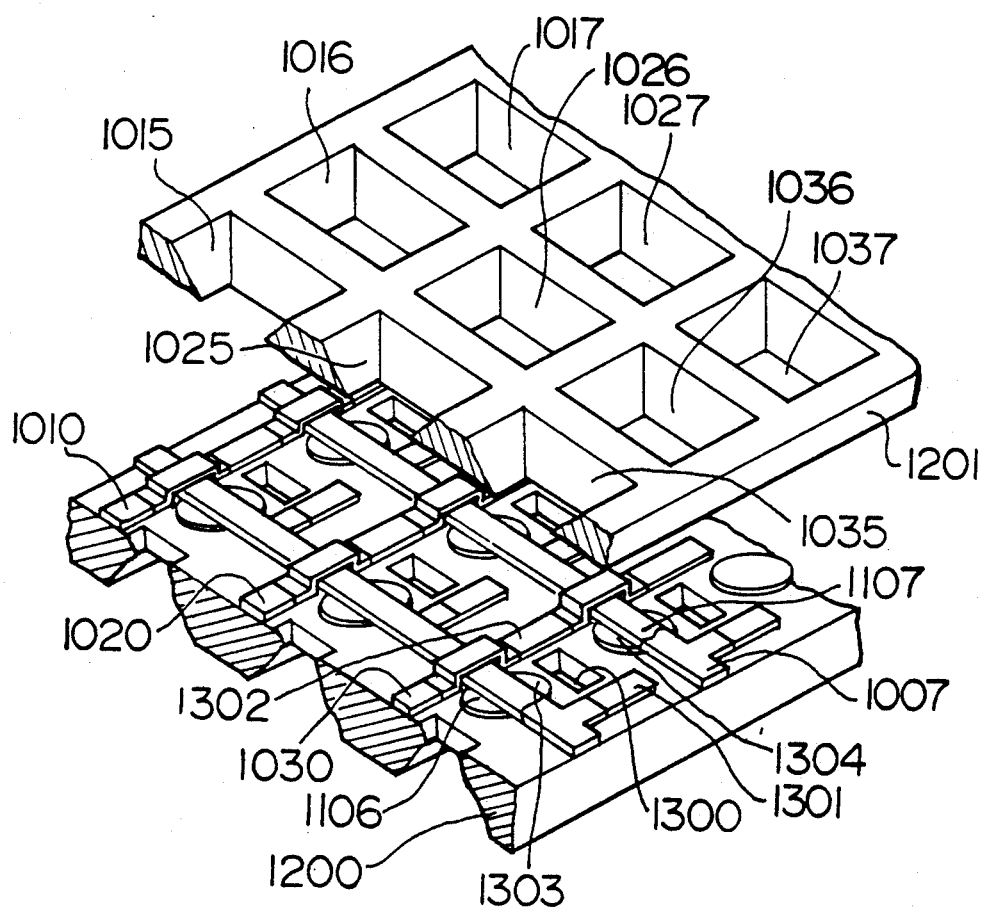
FIG. 10 is an enlarged perspective view of a cross section of an apparatus according to a still another embodiment of this invention.

FIG. 10 is a perspective view of the cross section of the microchamber plate having the wiring pattern shown in FIG. 9. The microchamber plate consists of a lower plate 1200 and an upper plate 1201. The lower plate 1200 has a number of the absorption ports having a size of 10 μm×80 μm for absorbing and positioning the cells. The upper plate 1201 has a number of microchambers at the positions corresponding to the positions of the absorption ports formed in the lower plate 1200. In FIG. 10, the lower plate 1200 is shown at a position away from the upper plate 1201, in order to clearly show the electrodes disposed at the boundary portion between these two plates 1200 and 1201. The lead wires 1006, 1007 and 1010 to 1030 have been made by using Au and have a thickness of 300 nm. The wiring pattern of this circuit is the same as that shown in FIG. 9. The crossing points of the wires in the circuit are coated with insulation layers consisting of $SiO_2$, in order to electrically insulate the wires from one another at the crossing points.

An explanation is given about the microchambers, taking the microchamber 1036 as an example. Along the longitudinal direction of the absorption port 1300 of the microchamber 1036, there are provided an electrode 1301 and another electrode 1302. The electrode 1301 is connected to the wiring 1006, and the electrode 1302 is connected to the wiring 1030. Projected insulator members 1303 and 1304 each consisting of $SiO_2$ are disposed along the lateral direction of the absorption port 1300. The two insulator members 1303 and 1304 are disposed in the manner that the absorption port 1300 is present between the insulator member 1303 and the insulator member 1304. When an electric voltage is loaded between the electrodes 1301 and 1302, the lines of the electrical force will be converged at the center of the absorption part 1300, due to the presence of the insulator members 1303 and 1304. Therefore, it is possible to effectively carry out an operation for loading an electric voltage on the cell pair held in touch with each other at the center of the absorption port, and also to carry out an operation for measuring the electric voltage.

In order to enhance the electrical S/N, it is important to converge the lines of the electrical force only at the area where the cells are present between the electrodes. For effecting the necessary detection, use may be made of a known Wheatstone Bridge circuit, wherein the three positions are occupied by the electrodes which do not allow the entrance of the biological cells, while the remaining one position is occupied by the chamber (impedance) to be measured, in consideration of the known impedance. An AC signal is loaded on the Wheatstone Bridge circuit, and a differential signal is detected, whereby the S/N can be improved.

For the purpose of suppressing any electrolysis of the solution, it is recommended to detect an impedance change at a high frequency of several MHz. It is preferred to employ the above-mentioned Wheatstone Bridge circuit. The electrodes for the detection can be disposed not only in the horizontal direction but also in the vertical direction, under such a condition that each pair of the cells are present between each set of the electrodes.

Figure 11:
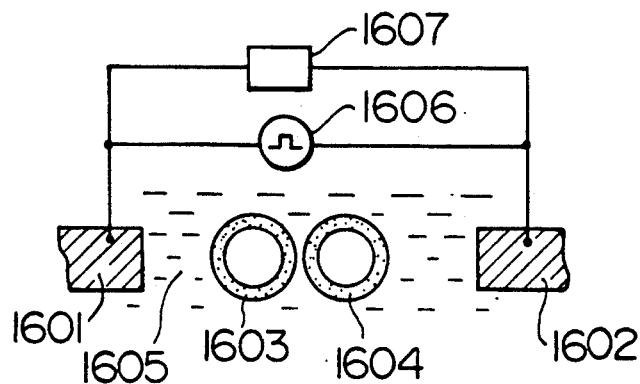
FIG. 11 is an enlarged schematic view of an electrode portion employed in a still another embodiment of this invention.
Figure 12:
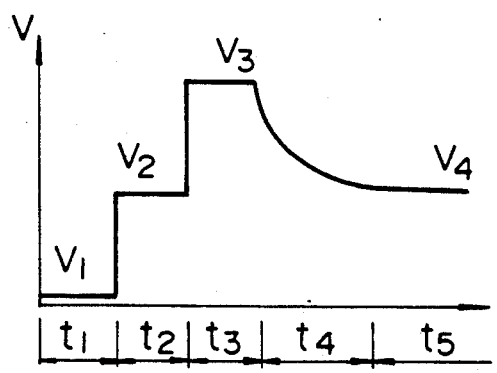
FIG. 12 is a graph illustrating the electrical characteristics observed in a cell fusion process.
Figure 13:
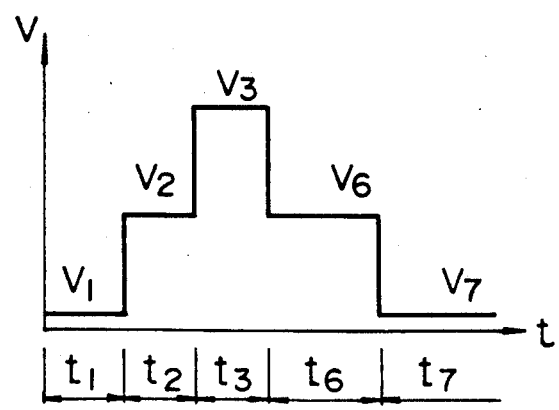
FIG. 13 is a graph illustrating the electric characteristics observed in a cell breakage process.

Next, with reference to FIGS. 11 to 13, an explanation will be made about an example wherein states and behaviors of cells present between one pair of electrodes are detected. FIG. 11 is an enlarged schematic view of an electrode portion in the example. In FIG. 11 it is shown that two different cells 1603 and 1604 are held in touch with each other between electrodes 1601 and 1602. These electrodes and the cells are soaked in the isotonic solution 1605. As disclosed in Saibou Kogaku (Cell Technology), Vol. 3, No. 6, 1988, pages 497 to 505, 0.5 mole isotonic sorbitol solution has a specific resistance of about 1 K$\Omega$·mm, and a cell membrane has a specific resistance of about 100 M$\Omega$·mm. In general, a cell membrane has a thickness of about 10 nm, and therefore fore has a resistance of about 1 K$\Omega$ in the direction of the thickness. In an embodiment of this invention shown in FIG. 11, the distance between the electrode 1601 and the electrode 1602 is 200 $\mu$m, and the electrodes each has a resistance of about 0.2 K$\Omega$. It is possible to determine the resistance of the cells present between the electrodes, if the width of the electrodes is smaller than the diameters of cells, or if there are disposed the insulator members 1303 and 1304 (FIG. 10) in order to converge the lines of the electrical force at the cells. A constant electrical voltage is loaded in a series of pulses from a power source 1606 to the position between the two electrodes 1601 and 1602, so that a detection circuit 1607 will detect the resistance of the cells depending on the thickness of the cell membranes, and will send the detected value of the resistance to an electrical control unit such as the unit 1905 (FIG. 7). When a lower pulse voltage is applied, any electrical decomposition of the isotonic solution will not occur. FIGS. 12 and 13 each are a graph illustrating the relationship between the electrical voltage and the time in the cell fusion experiments. FIG. 12 illustrates the characteristics of the cell fusion process. FIG. 13 illustrates the cell destroying process. In these graphs, the abscissa represents the time (t), and the ordinate represents the electrical voltage (V).

FIG. 12 shows that, when no cells are present between the two electrodes (time $t_1$), there is the electrical voltage $V_1$ relating only to the isotonic solution. When only one cell is present (time $t_2$), there is observed the electrical voltage $V_2$ which depends on the size of the cell. When two cells are held in touch with each other (time $t_3$), there is observed the electrical voltage $V_3$ which depends on the total length of the two cells. As the cell fusion begins and proceeds (time $t_4$), the shape of the two cells changes from a snowman-like shape into a spherical shape, so that the total length of the two cells decreases. As the cell fusion proceeds, the electrical voltage decreases. This process results in the forming of the hybrid cell showing an electric voltage of $V_4$.

FIG. 13 shows the characteristics directed to the number of the cells and also directed to the cell destruction. As for the periods of time $t_1$ to $t_3$, FIG. 13 shows the same phenomena as those shown in FIG. 12. When one of the two cells has been destroyed, a sudden change of the electrical voltage occurs as shown in FIG. 13, wherein the sudden voltage change is shown between the time $t_3$ and the time $t_4$. Such a sudden change up or down of the electrical voltage can be clearly distinguishable from a gradual voltage change observed in the course of a cell fusion process (FIG. 12; time $t_4$). The electrical voltage $V_6$ at the time $t_6$ corresponds to the resistance of the remaining cell after one of the two cells has been destroyed. The value of the voltage $V_6$ is nearly equal to that of the voltage $V_2$. If the remaining cell has also been destroyed, the electric voltage $V_7$ will be observed at the time $t_7$. The value of the voltage $V_7$ is virtually the same as that of the $V_1$.

It will be seen that the electric voltage will depend on the shape of electrodes, the concentration of the isotonic solution, the concentration of the electrolytes, the kind of biological cells, etc. However, after the experimental conditions has been initially settled, there is no great variation in the electric voltage measured.

It is also easy to determine other electrical values such as capacitance, electric permeability and the like by employing an appropriate electrical detection circuit.

An experiment was carried out wherein the effective diameter of the electrodes for the detection was 50 $\mu$m, the distance between the two electrodes was 200 $\mu$m and the electric voltage applied for the detection was 8 Vpp (1 MHz). When the cells with a diameter of about 40 $\mu$m were present, there was observed an electric voltage change of about 10 mV/cell.

The embodiments of this invention mentioned above are for the handling of biological cells having a size of 20 to 100 $\mu$m. It is also possible to handle cells having a different size, by properly designing the microchambers and the absorption ports of the microchamber plate. In the preparation of the absorption ports, it is necessary to effect a fine processing operation in the order of $\mu$m. The absorption ports may be prepared according to a patterning technique or an etching technique known in the art of the semiconductor processing technology. As the starting materials for the production of the microchamber plates, it is possible to use not only Si but also various glasses, resins, ceramics and the like, depending on the size, the accuracy, etc. required in individual cases.

As mentioned in the preceding paragraphs, it is possible according to this invention to exactly hold particles such as biological cells in a predetermined position, so that it is easy to carry out various operations including chemical treatments, material injection operations, marking operations, observation of proceeding of chemical rections and the like. Therefore, it is possible to provide a treatment apparatus, wherein a large amount of small particles can be exactly treated for a short period of time. It will be easily understood that, when the direction of the holding means has been made reverse, the relationship in specific gravity relative to cells between the first isotonic solution and the second isotonic solution should also be made reverse.

FIG. 4 is a view of an cell fusion processor employing a particle handling process according to this invention. This processor has the holding and supply means 31 to 35 for cells A and the holding and supply means 41 to 45 for other cells B, so that the cells A and B can be handled for a short period of time. The tank 61 and 81 are charged with the first isotonic solution having a greater specific gravity. The other tanks 63 and 83 are charged with the second isotonic solution having a smaller specific gravity. The tank 62 is filled with the cells A mixed with the first isotonic solution. The tank 82 is charged with the cells B mixed with the first isotonic solution. The container 54 is filled with the second isotonic solution 53. The levels of the water surfaces 132, 133, 134 and 135 are higher than the level of the water surface 131 (standard level), with the proviso that there is a level difference corresponding to a pressure of about 10 to 20 mmAq, to provide the necessary water head for the supply means 32 and 42.

The processor has the absorption devices by siphons 101, 111 and 121 as the means for applying an absorption pressure to the holding and treatment means. These absorption devices comprises the plates 102, 112 and 122, which are vertically movable by screws, and on which the containers filled with the second isotonic solution are placed. When the level of the water surface 136, 137 or 138 is lower than that of the standard water surface 131, an absorption pressure will generate. When the water surfaces 136 and 137 are kept at a level higher than the standard level of the water surface 131, a positive pressure will generate, whereby the held cells will be withdrawn therefrom. As the absorption process proceeds, the level of the above-mentioned four water surfaces will vary. In order to keep a contact absorption pressure at every time, it is necessary to vertically move the three plates 102, 112 and 122 under a control of a control system, wherein there is provided a pressure transducer or regulator (not shown) which can detect and regulate the absorption pressure of the holding and treatment means as a differential pressure relative to the standard level of the water surface of the container 54. Alternatively, it is possible to measure the water surface level of each container and to control the relative positions of containers without using such a pressure transducer or regulator. Furthermore, it is possible to provide an overflow line at a predetermined position and to supplement a small amount of the solution at times.

In the cell fusion processor according to this invention, wherein the cells are handled with the aid of a small pressure difference, it is observed that the handling efficiency of the cells may decrease if undesired micro bubbles have been trapped at the conduits, the holding means, the supply means or the treatment means disposed in the processor. It is necessary to remove such micro bubbles from the conduits and the like. For this purpose, it is possible to use a means (not shown) for supplying the isotonic solution through a pipe under pressurised conditions, to effect a forced absorbing operation, or to use an ultrasonic vibrator means. After the bubble removal, the valves 64 to 68, 84 to 88, 70, and 90 to 92 are closed, so that the preliminary operation is completed.

An explanation will be made about the procedures for the cell supply.

(i) The valves 67, 65, 87 and 85 are kept open for a predetermined period of time. Then the valves 67 and 87 are closed, and furthermore the valves 65 and 85 are closed, so that the cells A and B stay in the conduits 69 and 89, respectively.

(ii) The valve 64 or 84, the valve 68 or 88 and the valve 70 or 90 are kept open for a predetermined period of time, to send the cells A or B to the supply means 32 or 42. After a predetermined amount of the cells has been supplied, the valve 68 or 88 is closed.

(iii) The valve 71 or 91 is kept open, whereby the cells A or B which are floating at the gap 33 or 43 of the supply means are absorbed and held in the holding means 31 or 41. Under the absorbing conditions, the operations (ii) are repeated, and then the valve 64 or 84 is closed.

(iv) The valve 66 or 86 is kept open for predetermined period of time to sink the excess cells present at the gap 33 or 43 of the supply means, and to wash away the excess cells. After the wash away operation has been effected for a predetermined period of time, the holding means 31 or 41 is ascended at a low speed, and the valve 66 or 86 is closed.

(v) The holding means 31 or 41 is moved to a position near the treatment means 51, and an exact positioning operation of the holding means is carried out. Then the valve 92 is opened, and the treatment means is subjected to an absorption operation. The absorption system 101 or 112 is ascended by a predetermined distance. Then the holding means is kept under a positive pressure to transfer the held cells to the treatment means. After the transfer operation, the valve 71 or 91 is closed.

It is probable that the activity of the transferred cells or the fused cells will decrease if the cells are in contact with the side walls of the treatment means for a long period of time. In order to avoid such activity decrease of the cells, use is made of a means 152 for applying a slighly high pressure through a conduit 151, whereby the cells can be slightly floated off the side walls by a distance of about 10 to 90 μm at an interval of several seconds. The slightly pressurizing means 152 may be so designed that an elastic pipe is hammered at a small stroke with a piston which is reciprocally moved at a controlled speed.

FIG. 5 illustrates the manner of transferring the cells A and B to the treatment means, and also shows the relative positions of the several means employed, together with the arrow marks indicating the flow directions of the streams supplied or withdrawn. According to this invention, the two holding means 31 and 41 are integrated with each other with the aid an arm member (not shown). These holding means can be simultaneously moved not only in the vertical direction by means of a vertical drive mechanism (not shown), but also in the horizontal direction by a horizontal drive mechanism (not shown).

Figure 5A:
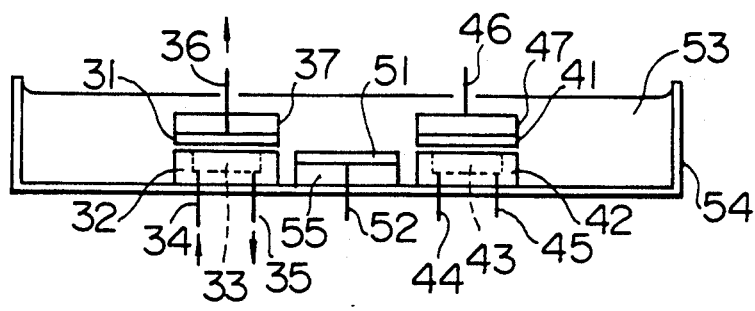
FIGS. 5(a) to (e) are views illustrating the operations of the main portion of the processor shown in FIG. 4.
Figure 5B:
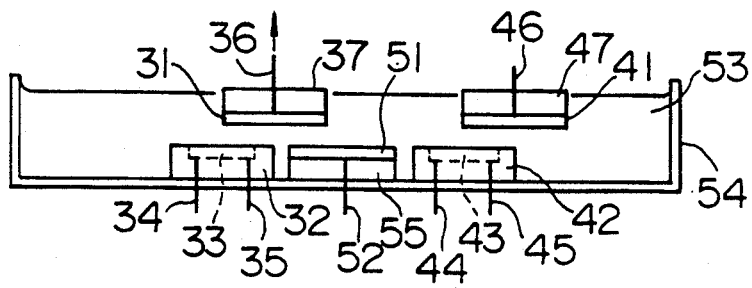
Figure 5C:
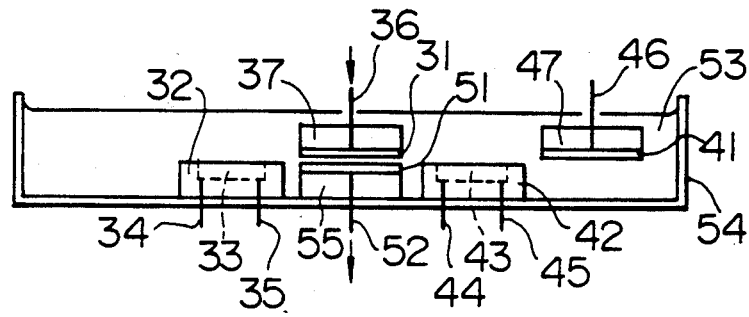
Figure 5D:
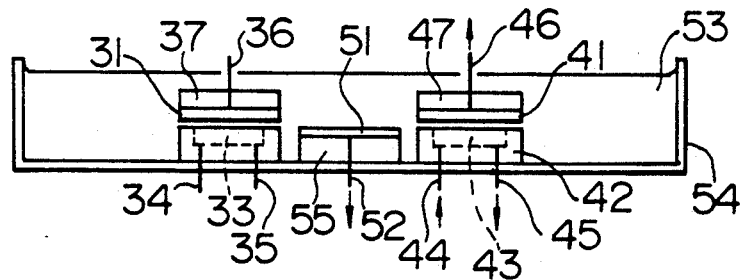
Figure 5E:
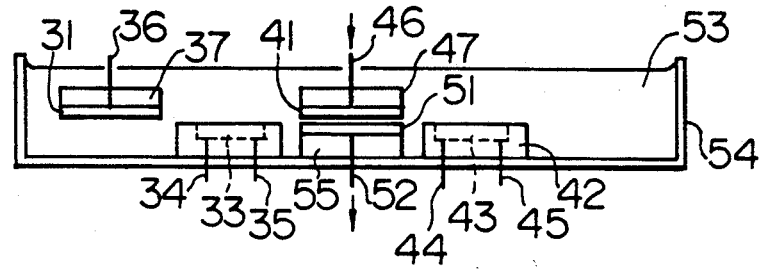

FIG. 5(a) shows a step of holding the cells A in the holding means 37 under an absorption pressure. FIG. 5(b) illustrates a step, wherein the holding means 31 which contains the cells A held therein is ascended by about 1 mm, and then moved rightwards to a position near the treatment means. FIG. 5(c) shows a step, wherein a positioning operation is effected relative to the treatment means, and then the cells A are transferred to the treatment means. FIG. 5(d) shows a step of holding the cells B in the holding means 41 under an absorption pressure. FIG. 5(e) illustrates a step, wherein the cells B are transferred to the treatment means which already contains the cell A transferred thereto.

After the transfer operation has been completed, the treatment means contains a number of pairs of the cells A and B. These cell pairs are together subjected to a cell fusion treatment, so that it is possible to obtain only the fused cells formed from the cells A and B.

It is easy to vary the shape and size of the holding means, the supply means and the treatment means, depending on the size of particles handled.

The cell fusion apparatus according to this invention can also be used as a 'cell treatment apparatus for a chemical treatment, a culture treatment, etc.

It is also possible to provide a gene injection processor, wherein the microchambers which contain cells held therein are placed in a gene-suspended liquid, micro holes are formed in the cell walls by means of a radiation of an electrical voltage or a laser ray or an X-ray, and then the genes are injected into the cells.

Furthermore, if blood is used as the particles, it is possible to count the number of the blood cells held at the microchambers, whereby the number of the blood cells per unit volume of the liquid can be determined, so that the blood cell count can be determined accordingly. Furthermore, it is possible to provide a blood treatment apparatus, wherein an electrical voltage is loaded on the blood cells held in the microchambers, whereby a shape change of the blood cells will occur, so that it is possible to determine the blood cell deformation ability of the blood sample. The results of this measurement can be employed in the diagnosis of the patient concerned.

When particles are handled and held at the fixed positions according to this invention, it is preferred to avoid any presence of air bubbles on the microchambers and the absorption ports of the microchamber plate. It is recommended that the presence or absence of air bubbles should be detected beforehand by measuring the electrical potential between the electrodes of each microchamber. After that, an operation may be effected to remove such air bubbles from the apparatus. It is also possible to make an interpretation of the air bubbles present in the apparatus.

What is claimed is:

1. A method for transferring biological cells to a plurality of microchambers arranged in a pattern, which comprises supplying the biological cells to a first solution in contact with a plurality of holding means including absorption ports for retaining individual biological cells, said first solution having a specific gravity which causes the biological cells to move towards said holding means; holding an individual biological cell at each of said absorption ports of said holding means; removing other cells not held by said absorption ports of said holding means by supplying a second solution, said second solution causing the other cells to move away from said holding means and transferring the held biological cells within the absorption ports of said holding means to the plurality of microchambers arranged in a pattern.

2. A method for transferring biological cells to a plurality of microchambers arranged in a pattern, according to claim 1, wherein the first solution has a specific gravity greater than that of said cells and is supplied under the holding means to cause said cells to ascend to the holding means; and then some of the cells are individually held by the plurality of absorption ports of said holding means; thereafter, the second solution having a specific gravity smaller than that of said cells is supplied under the holding means to cause the other cells not held to descend away from said holding means; and the cells held in the absorption ports of said holding means are transferred to the microchambers, said holding means being arranged in a pattern corresponding to the pattern of said microchambers.

3. A method for transferring biological cells to a plurality of microchambers arranged in a pattern, according to claim 1, wherein the first solution has a specific gravity smaller than that of said cells and is supplied over the holding means to cause said cells to descend to the holding means; and then some of said cells are individually held by the plurality of absorption ports of said holding means; thereafter, the second solution having a specific gravity greater than that of said cells is supplied over the holding means to cause the other cells not held to ascend away from said holding means; and the cells held in the absorption ports of said holding means are transferred to the microchambers, said holding means being arranged in the pattern corresponding to the pattern of said microchambers.

* * * * *